(12) United States Patent
Volkmuth et al.

(10) Patent No.: US 9,629,579 B2
(45) Date of Patent: Apr. 25, 2017

(54) LANCING DEVICE FOR TAKING BLOOD SAMPLES

(71) Applicant: Gerresheimer Regensburg GmbH, Regensburg (DE)

(72) Inventors: Julia Volkmuth, Maxhuette-Haidhof (DE); Andreas Eder, Regensburg (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 228 days.

(21) Appl. No.: 14/046,395

(22) Filed: Oct. 4, 2013

(65) Prior Publication Data

US 2014/0100481 A1  Apr. 10, 2014

(30) Foreign Application Priority Data

Oct. 4, 2012  (DE) .................. 10 2012 019 400

(51) Int. Cl.
*A61B 5/151*   (2006.01)
*A61B 5/15*    (2006.01)

(52) U.S. Cl.
CPC ........ *A61B 5/15144* (2013.01); *A61B 5/1519* (2013.01); *A61B 5/150022* (2013.01); *A61B 5/15077* (2013.01); *A61B 5/15113* (2013.01); *A61B 5/15117* (2013.01); *A61B 5/15194* (2013.01); *A61B 5/150259* (2013.01); *A61B 5/150412* (2013.01); *A61B 5/150503* (2013.01); *A61B 5/150786* (2013.01); *A61B 5/150824* (2013.01); *A61B 5/150832* (2013.01)

(58) Field of Classification Search
CPC ............ A61B 5/15192; A61B 5/15144; A61B 5/1519

See application file for complete search history.

(56) References Cited

U.S. PATENT DOCUMENTS 5,879,311 A   3/1999  Duchon et al.
6,045,567 A   4/2000  Taylor et al.
(Continued)

FOREIGN PATENT DOCUMENTS

EP   2050393 A1   4/2009

OTHER PUBLICATIONS

Examination Report issued on May 24, 2013, from the German Patent Office for German Patent Application No. 10 2012 019 400.5.
(Continued)

*Primary Examiner* — Devin Henson
*Assistant Examiner* — Matthew Kremer
(74) *Attorney, Agent, or Firm* — Lathrop & Gage LLP

(57) ABSTRACT

A lancing device (1) for taking blood samples comprises a housing (2), an axially displaceable lancet holder element (32) for holding a replaceable lancet (12), and a drive unit (30) comprising at least a lancing spring element (31) for driving the axially displaceable lancet holder element (32) in a lancing direction (18). The lancing device further comprises a tensioning carriage part (26) which can be fixed in a tensioning position (36) for tensioning the lancing spring element (31). The fixable tensioning carriage part (26) is temporarily axially fixed in this tensioning position (36) by means of a latching apparatus (35) which can be latched to the axially displaceable lancet holder element (32).

20 Claims, 5 Drawing Sheets

(56) References Cited

U.S. PATENT DOCUMENTS

| | | |
|---|---|---|
| 6,730,046 B1 * | 5/2004 | Hamamoto .......... A61B 5/1411 600/583 |
| 8,827,925 B2 | 9/2014 | Butz et al. |
| 8,828,039 B2 | 9/2014 | Butz et al. |
| 8,986,258 B2 | 3/2015 | Michaelis |
| D740,422 S | 10/2015 | Herfort |
| 9,314,200 B2 | 4/2016 | Vogl et al. |
| 2006/0100656 A1 | 5/2006 | Olson et al. |
| 2008/0195132 A1 * | 8/2008 | Schraga ............... A61B 5/1411 606/182 |
| 2009/0105613 A1 | 4/2009 | Nishiuchi |
| 2009/0125048 A1 * | 5/2009 | Robbins ............... A61B 5/1411 606/182 |
| 2010/0094324 A1 | 4/2010 | Huang et al. |
| 2010/0217105 A1 * | 8/2010 | Yodfat et al. ................. 600/365 |
| 2014/0081173 A1 | 3/2014 | Volkmuth et al. |
| 2014/0100482 A1 | 4/2014 | Volkmuth et al. |
| 2014/0128897 A1 | 5/2014 | Butz et al. |
| 2014/0155926 A1 | 6/2014 | Volkmuth et al. |

OTHER PUBLICATIONS

Examination Report issued on May 28, 2013, from the German Patent Office for German Patent Application No. 10 2012 019 404.8.
Examination Report issued on May 27, 2013, from the German Patent Office for German Patent Application No. 10 2012 019 401.3.
European Search Report issued on Jan. 28, 2014, from the European Patent Office for European Patent Application No. 13186675.8, 5 pages.
Chinese Examination Report, dated Apr. 28, 2015, in Chinese patent application serial No. 201310465440.X, 1 page.

* cited by examiner

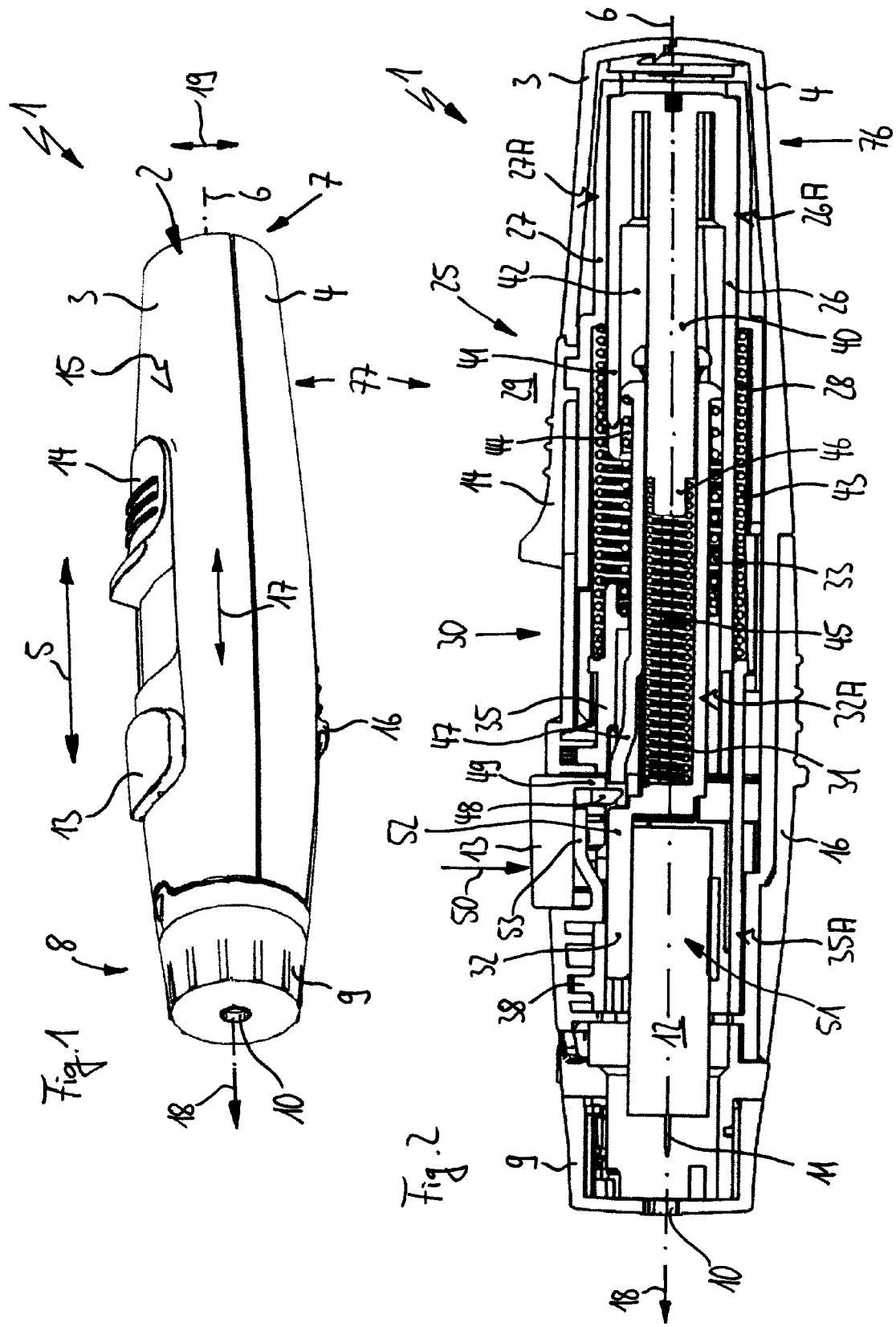

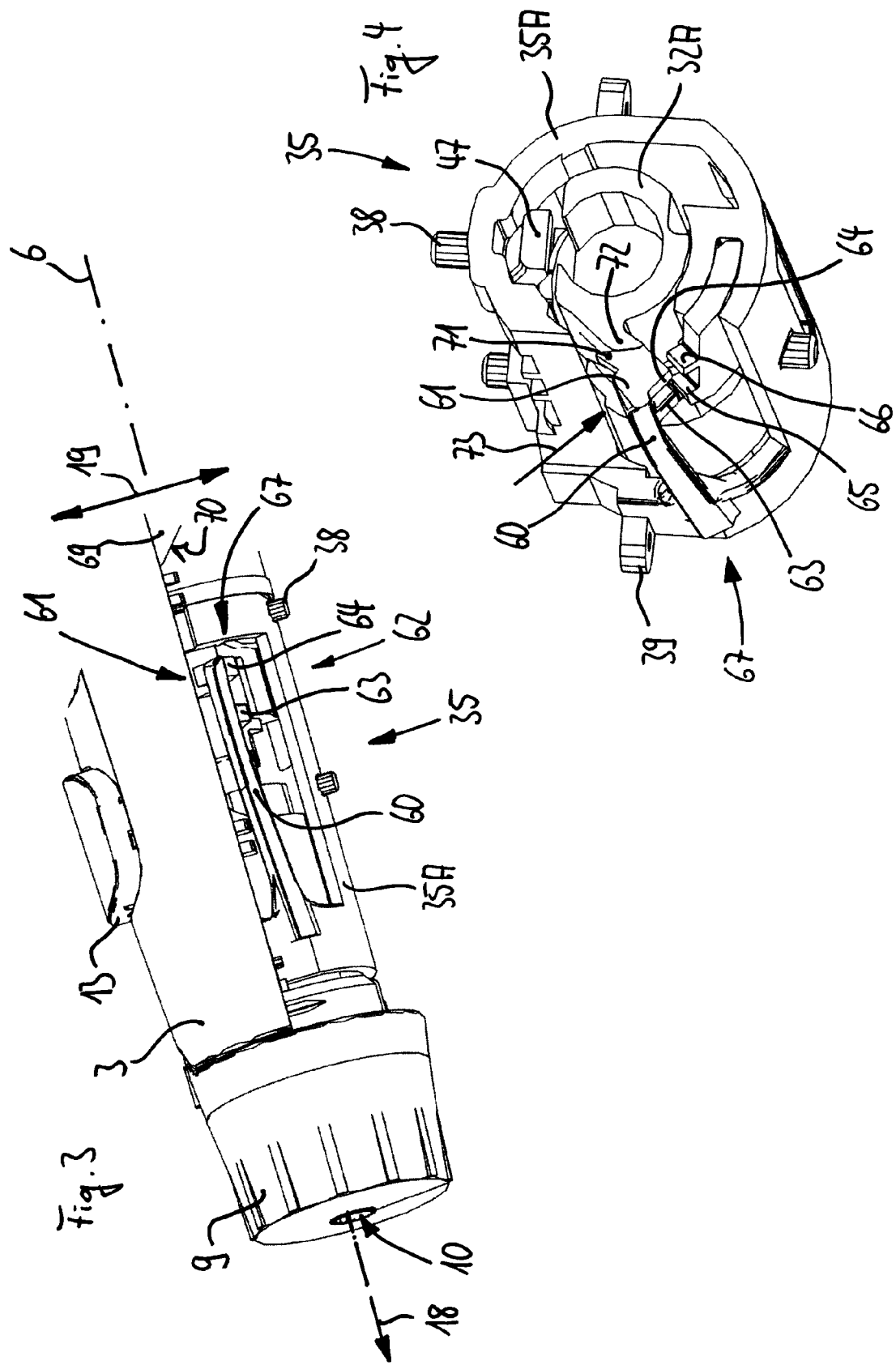

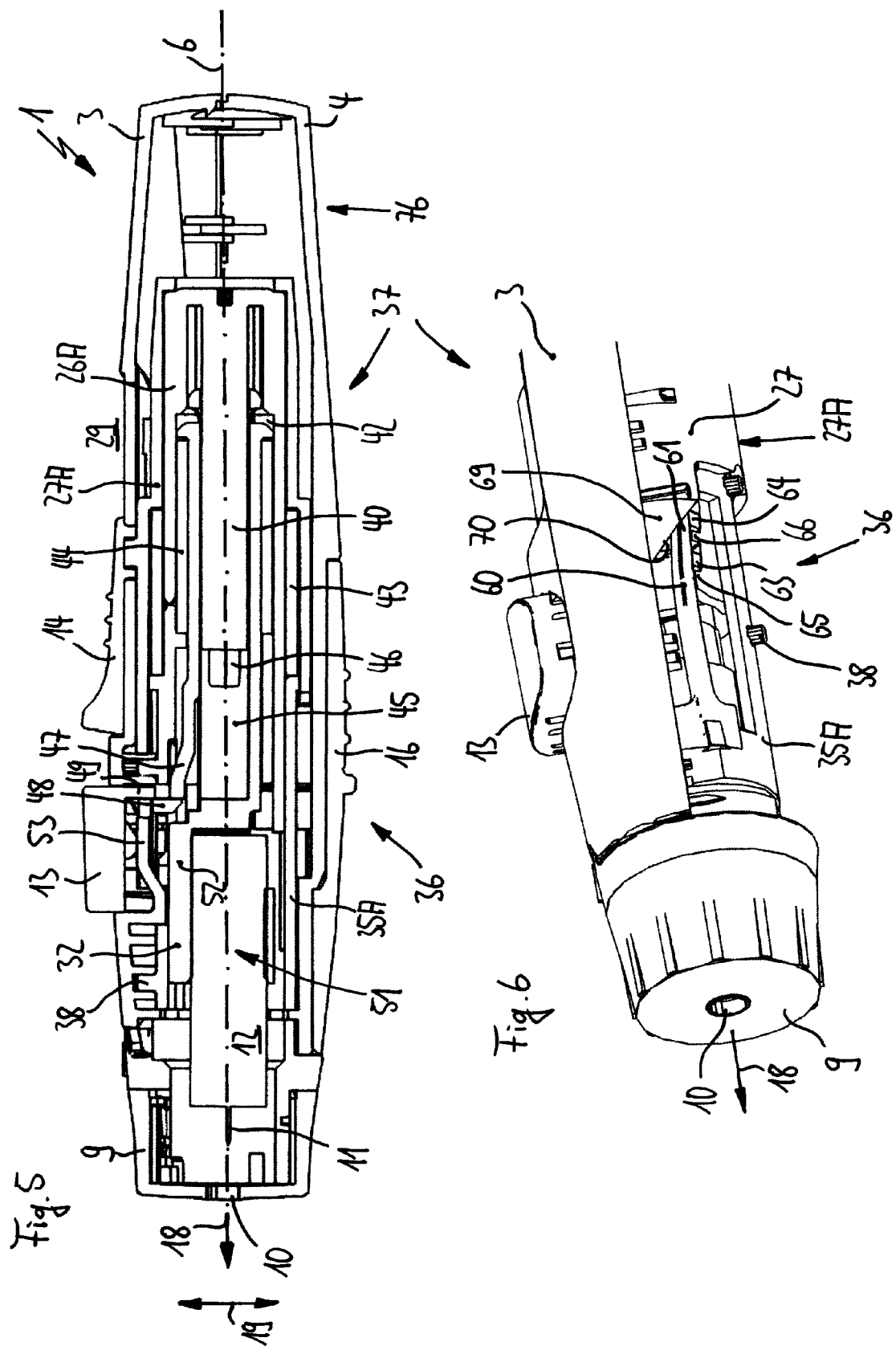

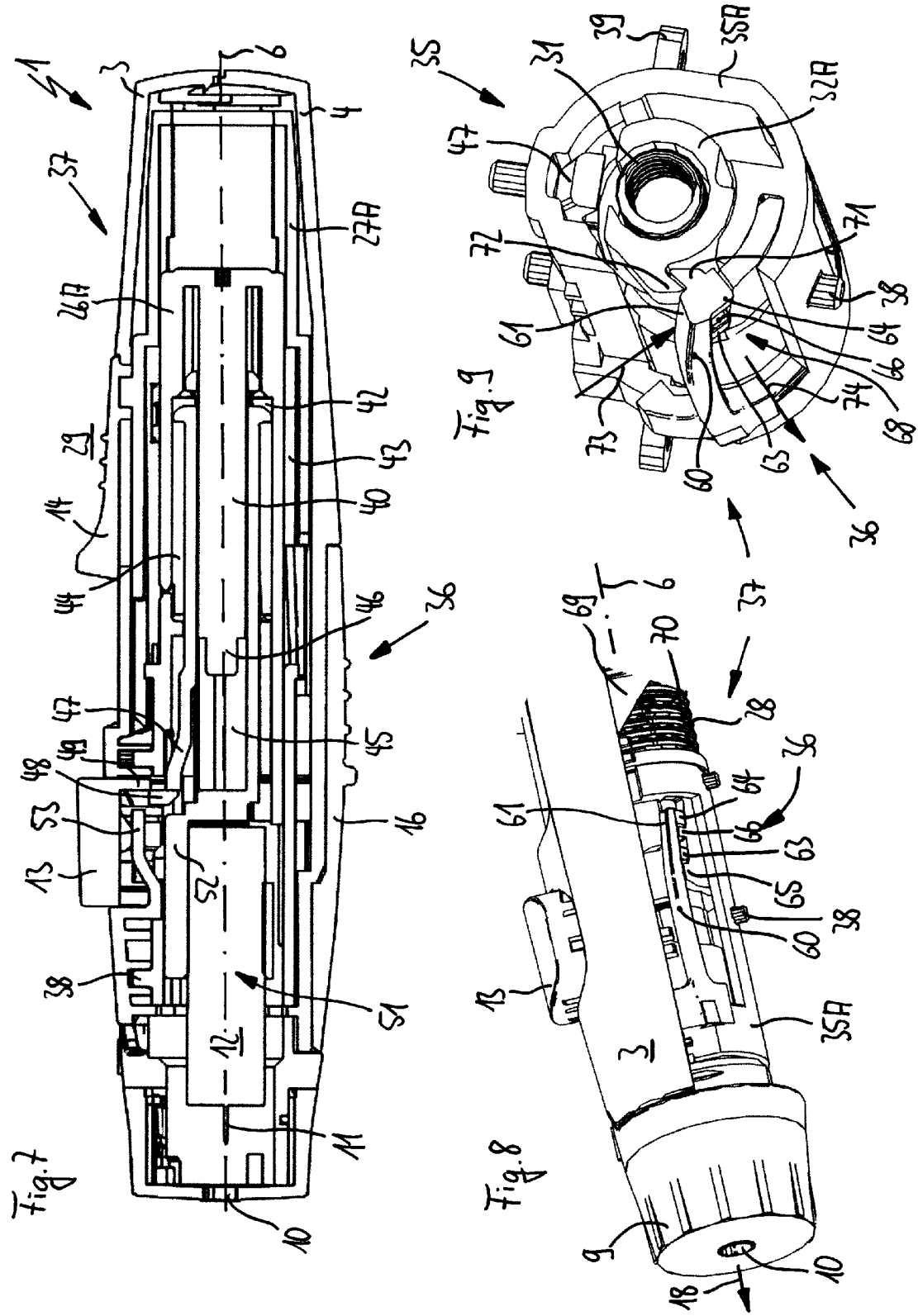

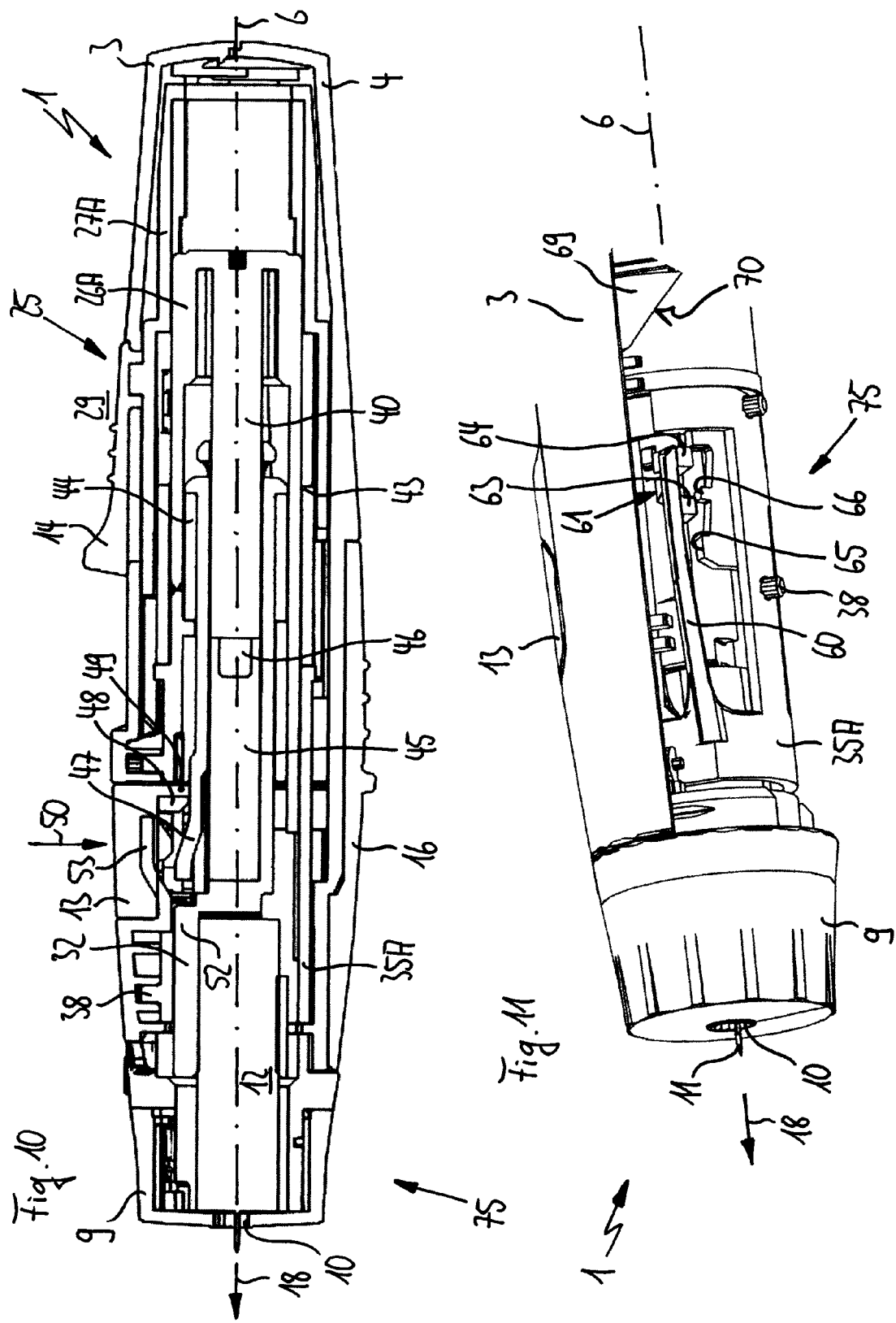

LANCING DEVICE FOR TAKING BLOOD SAMPLES

CROSS REFERENCE TO RELATED APPLICATIONS

This application claims the benefit of and priority to German Application No. 10 2012 019 400.5, filed on Oct. 4, 2012, which is hereby incorporated by reference in its entirety.

DESCRIPTION

The invention relates to a lancing device for taking blood samples, comprising a housing, an axially displaceable lancet holder element for holding a replaceable lancet, a drive unit comprising at least a lancing spring element for driving the axially displaceable lancet holder element in a lancing direction, and a tensioning carriage part which can be fixed in a tensioning position for tensioning the lancing spring element.

Generic lancing devices comprising a drive unit made up of in particular two spring elements connected in series are known from the prior art. In a lancing device of this type, a front lancing spring element, that is to say a spring element facing a lancet holder to be accelerated, ensures acceleration of a lancet held by this lancet holder during a lancing procedure. A rear return spring element, that is to say a spring element further from the lancet holder to be accelerated, ensures a return movement of the lancet holder after the lancing procedure. These two spring elements which interact in this way make it possible reliably to avoid excessive critical reverberation of the lancet holder on the lancing device after a lancing procedure. A drawback of these or similar known lancing devices is an often structurally complex design of the mechanics, which also makes handling of lancing devices of this type more difficult.

The problem addressed by the present invention is to simplify generic lancing devices in terms of their structural design and also in terms of their handling.

The problem addressed by the invention is solved by a lancing device for taking blood samples, comprising a housing, an axially displaceable lancet holder element for holding a replaceable lancet, a drive unit comprising at least a lancing spring element for driving the axially displaceable lancet holder element in a lancing direction, and a tensioning carriage part which can be fixed in a tensioning position for tensioning the lancing spring element, the fixable tensioning carriage part being temporarily axially fixed in this tensioning position by means of a latching apparatus which can be latched to the axially displaceable lancet holder element.

Because the tensioning carriage part which can be fixed in the tensioning position is temporarily axially fixed in this tensioning position by means of the latching apparatus which can be latched to the axially displaceable lancet holder element, the mechanical design of the lancing device is greatly simplified by a reduction in components.

In particular, a new release option with regard to the lancing procedure is achieved as a result, significantly simplifying the operation of the present lancing device. Improved handling for a user is made possible as a result, owing to which a significantly improved lancing result is also achieved.

It will be understood that the present drive unit can be configured in a variety of ways. It advantageously comprises at least two spring elements, including a lancing spring element for accelerating the axially displaceable lancet holder element in the lancing direction and a return spring element for accelerating the axially displaceable lancet holder element counter to the lancing direction.

In particular as a result, overshooting of the spring elements is advantageously not necessary, since a forward movement during the lancing procedure and the subsequent return movement after the actual lancing procedure are performed by two separate spring elements.

The spring elements used in this case preferably comprise helical spring elements. In this respect, the tensioning carriage part which can be fixed in the tensioning position is preferably a tensioning spring element carriage part.

In the present case, at least the axially displaceable lancet holder element moves in translation in the lancing direction in order to perform a lancing procedure. It moves in translation counter to this lancing direction in order to displace the lancet back into the housing.

Another structural advantage is that the fixable tensioning carriage part is mounted in the housing such that it can also move along the displacement axis in order that it can be displaced into or out of the tensioning position.

In this respect, this lancing direction also forms the displacement axis along which or in the direction of which in particular the axially displaceable lancet holder element moves in translation inside the housing.

The axially displaceable lancet holder element thus ideally forms in a structurally simple manner a lancing carriage part inside the housing of the present lancing device.

An advantageous variant provides that the latching apparatus comprises a latching arm element which can be deflected radially in relation to the lancing direction and which interacts with a positive fit with the axially displaceable lancet holder element during fixing of the fixable tensioning carriage part in the tensioning position. As a result, the latchable latching apparatus can be implemented in a structurally particularly simple manner.

A deflectable latching arm element of this type can be bent in a structurally simple, ideally elastic manner.

The elastically deflectable latching arm element is preferably elastically bendable at least in two different paths. In this case, the two different paths preferably extend at right angles to each other.

In this respect, the elastically deflectable latching arm element is repeatedly bendable. Another advantageous variant provides that the latching apparatus which can be latched to the axially displaceable lancet holder element comprises means for fixing the fixable tensioning carriage part. This is particularly advantageous when the latchable latching apparatus is not directly assigned to the fixable tensioning carriage part.

In this connection, it is particularly advantageous for the latchable latching apparatus to comprise a latching arm element which can be deflected radially in relation to the lancing direction and which comprises means for fixing the fixable tensioning carriage part to the latching arm element, in particular with a positive fit.

In this connection, the means for fixing the fixable tensioning carriage part can be in a variety of forms. For example, they include tongue elements or groove elements of a tongue and groove joint, which can interact with the corresponding counter elements on the fixable tensioning carriage part when this is in the tensioning position. As a result, in particular means for axially fixing the fixable tensioning carriage part can be implemented in a structurally simple manner.

A preferred variant further provides that the latching apparatus is arranged in the housing such that a latching arm element which can be deflected radially in relation to the lancing direction is arranged such that it can be disengaged radially by a translatory change in position of the axially displaceable lancet holder element in the lancing direction, such that the fixable tensioning carriage part can be displaced in translation from the tensioning position into a relaxed position with the help of a compression spring element. As a result, it is possible in a structurally simple manner to return the fixable tensioning carriage part to its original resting position or relaxed position in order to reliably prepare the lancing device for a new lancing procedure, for example for a safe change of lancet.

It is also advantageous for the latching apparatus to interact with the fixable tensioning carriage part on the basis of a relative axial position of the axially displaceable lancet holder element in relation to the housing. A very simple design of the mechanics can be achieved as a result.

A further structural simplification can be achieved when the latching apparatus comprises a sleeve part which radially surrounds the axially displaceable lancet holder element externally at least in part.

Structurally simple interaction between the latchable latching apparatus and the axially displaceable lancet holder element can be improved significantly when the axially displaceable lancet holder element comprises a latching rib which can be engaged from behind by the latchable latching apparatus and which extends axially on the displaceable lancet holder element.

The latching rib which can be engaged from behind is advantageously positioned on the axially displaceable lancet holder element such that said rib is out of reach of the deflectable latching arm element of the latchable latching apparatus when the axially displaceable lancet holder element is in or not far short of its lancing end position.

In this respect, it is advantageous for the latching apparatus to comprise means for interlocking with the axially displaceable lancet holder element. For example, the interlocking means comprise at least a latching projection element which can engage the latching rib from behind.

In particular, operation of the lancing device can also be made significantly easier when a tensioning unit comprising the fixable tensioning carriage part comprises a further tensioning carriage part for displacing the fixable tensioning carriage part, the further tensioning carriage part comprising an engagement element for radial engagement of the latching apparatus which can be latched to the axially displaceable lancet holder element.

This further tensioning carriage part can advantageously be slid manually along the displacement axis in the lancing direction by means of a slide which is accessible outside the housing, such that the fixable tensioning carriage part can be displaced into the tensioning position manually and in a structurally simple manner.

In this connection, the slide is ideally mounted on the housing such that it can be slid axially in the longitudinal extension of the lancing device.

The engagement element assigned to the further tensioning carriage part can also have a variety of structural forms. With regard to a preferred design variant, it is advantageous for the engagement element to comprise a sliding guide face which is inclined in relation to the lancing direction. As a result it is possible in a structurally very compact manner to switch a movement of the further tensioning carriage part directed axially along the displacement axis into a movement of the latchable latching apparatus or the deflectable latching arm element directed radially in relation to the displacement axis.

The present lancing device can generally be constructed in an even more compact manner, and thus again in a manner which is easier to handle, when the axially displaceable lancet holder element, the fixable tensioning carriage part or the further tensioning carriage part of the tensioning apparatus each comprise a sleeve part.

In this connection, it is particularly advantageous for individual ones of the sleeve parts to be arranged in the housing such that they can be slid along the displacement axis, for example in a telescoped manner.

In this respect, it is extremely advantageous for the axially displaceable lancet holder element, the fixable tensioning carriage part and/or the further tensioning carriage part to have a common displacement axis.

It is also particularly advantageous for the present kinematics of the drive unit in terms of the tensioning procedure and the actual lancing procedure to be implemented substantially by the two tensioning carriage parts of the tensioning unit and by the lancing carriage part, which are arranged such that they can be telescoped at least in part.

A further structural simplification of the lancing device can be achieved when the lancing device comprises a two-part housing comprising an upper shell part and a lower shell part on which at least the further tensioning carriage part is guided directly in translation.

All in all, extremely good ergonomic handling can be achieved with the lancing device according to the invention owing to the simple tensioning of the lancing spring element by sliding of the slide.

In addition, the lancing device is distinguished by simple release of the lancet holder element or the lancing carriage part by radial pressing of the release element, since the axially displaceable lancet holder element comprises a radially inwardly deflectable finger clip element which, when the lancing device is in the unreleased state, is supported against a radially inwardly projecting housing web, preventing axial displacement of the lancet holder element in the lancing direction until the release element has been pressed radially into the housing.

In this respect, sequential release of the axially displaceable lancet holder element and of the fixable tensioning carriage part is thus achieved, which release requires only a single manual action by the user, namely a single-stage actuation of the release element. This simplifies significantly the handling of the present lancing device.

Since the present latching apparatus and in particular the elastically bendable or elastically deflectable latching arm element thereof comprises not only means for fixing the fixable tensioning carriage part but in addition advantageously also means for interlocking, preferably in the form of a latching projection element, with the axially displaceable lancet holder element, the mechanics of the present lancing device can have a extremely simple form.

Further advantages, aims and properties of the present invention will be described by way of the appended drawings and the following description, in which by way of example a lancing device according to the invention for taking blood samples, comprising an axially displaceable lancet holder element and comprising a tensioning carriage part which can be fixed temporarily by a latching apparatus which can be latched to the axially displaceable lancet holder element, is shown and described.

In the drawings:

FIG. 1 shows schematically a plan view of a lancing device for taking blood samples, comprising a tensioning carriage part which can be fixed temporarily by a latching apparatus which can be latched to an axially displaceable lancet holder element, in a resting state;

FIG. 2 shows schematically a longitudinal sectional side view of the lancing device from FIG. 1 in the resting state;

FIG. 3 shows schematically a front detailed side view of an unlatched latching apparatus of the lancing device according to FIG. 2;

FIG. 4 shows schematically a perspective detailed rear view of the unlatched latching apparatus of the lancing device from FIGS. 1 to 3;

FIG. 5 shows schematically a further longitudinal sectional side view of the lancing device from FIGS. 1 to 4 in a tensioned state with a latched latching apparatus, in which a further tensioning carriage part for axial displacement of the fixable tensioning carriage part is in a front sliding position;

FIG. 6 shows schematically a further front detailed side view of the latched latching apparatus of the lancing device according to FIG. 5;

FIG. 7 shows schematically yet another longitudinal sectional side view of the lancing device from FIGS. 1 to 6 in the tensioned state, in which the further tensioning carriage part for axial displacement of the fixable tensioning carriage part is back in a rear starting position;

FIG. 8 shows schematically a front detailed side view of the latched latching apparatus of the lancing device according to FIG. 7;

FIG. 9 shows schematically a further perspective detailed rear view of the latched latching apparatus of the lancing device from FIGS. 1 to 8 in the tensioned state;

FIG. 10 shows schematically another longitudinal sectional side view of the lancing device from FIGS. 1 to 9 in a released state; and FIG. 11 shows schematically a further front detailed side view of the lancing device according to FIG. 10.

The lancing device 1 shown in FIGS. 1 to 11 is intended for taking a blood sample. The lancing device 1 comprises a two-part housing 2 comprising an upper shell part 3 and a lower shell part 4.

The lancing device 1 extends with a longitudinal extension 5 along a longitudinal axis 6 from an end region 7 of the lancing device 1 to a head region 8 of the lancing device 1, a screw cap 9 having a feed-through opening 10 for a lancing needle 11 of a replaceable lancet 12 (see for example FIG. 2) of the lancing device 1 being screwed into the housing 2 in this head region 8 of the lancing device 1.

On the upper shell part 3, a release pressure element 13 and a tensioning slide element 14, which both project radially beyond the outer face 15 of the housing 2 such that they are easily manually accessible, are located radially adjacent to the longitudinal axis 6.

On the lower shell part 4, an ejector slide element 16, which likewise projects radially beyond the outer face 15 of the housing 2 so as also to be manually accessible without difficulty, is located radially adjacent to the longitudinal axis 6.

While the tensioning slide element 14 and the ejector slide element 16 are displaceable axially along the longitudinal axis 6 in axial directions 17 and in particular in the lancing direction 18, the release pressure element 13 is displaceable radially in relation to the longitudinal axis 6 in radial directions 19.

In this connection, the tensioning slide element 14 is a component of a tensioning unit 25 of the lancing device 1, the tensioning unit 25 also comprising at least a fixable tensioning carriage part 26 for tensioning the lancing device 1, a further tensioning carriage part 27 for axial displacement of the fixable tensioning carriage part 26, and a tensioning carriage spring element 28 for displacing the further tensioning carriage part 27 back into a rear starting position 29 after a lancing procedure.

The fixable tensioning carriage part 26 and the further tensioning carriage part 27 are not fixed rigidly to one another but are mounted such that they can be slid axially relative to one another. However, the fixable tensioning carriage part 26 is entrained by the further tensioning carriage part 27 when the further tensioning carriage part 27 is displaced in the lancing direction 18 by means of the tensioning slide element 14.

In this connection, both the fixable tensioning carriage part 26 and the further tensioning carriage part 27 are designed as sleeve parts 26A and 27A, the sleeve part 26A of the fixable tensioning carriage part 26 being mounted such that it can be slid axially inside the further tensioning carriage part 27, at least in part, and the sleeve part 27A of the further tensioning carriage part 27 being mounted such that it can be slid axially in the upper and lower shell parts 3 and 4 of the two-part housing 2.

The further tensioning carriage part 27 is connected with a positive fit to the tensioning slide element 14 (see in particular FIG. 2), whereby said tensioning carriage part can be actuated manually by means of the tensioning slide element 14.

In addition, the lancing device 1 has a drive unit 30 comprising at least a lancing spring element 31 for accelerating an axially displaceable lancet holder element 32 in a lancing direction 18 and a return spring element 33 for accelerating the axially displaceable lancet holder element 32 counter to the lancing direction 18 after a completed lancing procedure.

In the present case, the axially displaceable lancet holder element 32 is also designed as a sleeve part 32A, in which the sleeve part 27A of the fixable tensioning carriage part 27 can be slid axially, at least in part, upon tensioning of the lancing device 1.

In addition, in this connection the sleeve part 32A of the axially displaceable lancet holder element 32 can be slid axially into the sleeve part 27A of the fixable tensioning carriage part 27, at least in part, whereby a lancing device 1 which is very compact and thus advantageously easy to handle can be provided.

The lancing device 1 also comprises a latching apparatus 35 which as a sleeve part 35A in the two-part housing 2 is rigidly fixed to the upper and lower shell parts 3 and 4 and is thus axially secured against sliding.

By means of the latching apparatus 35, the fixable tensioning carriage part 26 slid in the lancing direction 18 can be fixed in a tensioning position 36 (see in particular FIGS. 5 to 9), as described in more detail below. According to the invention, the latching apparatus 35, in such a tensioned state 37 of the lancing device 1, is latched to the displaceable lancet holder element 32 such that, upon axial displacement of the lancet holder element 32 in the lancing direction 18, the latching apparatus 35 unlatches and thus the tensioning carriage part 26 fixed to the latching apparatus comes free and can be displaced rearwards towards the end region 7 by spring force of the lancing spring element 31.

Advantageously, the latching apparatus 35 simultaneously also serves as a mounting and guiding apparatus for axial and radial mounting of an axially displaceable lancet holder element 32, whereby the lancing device 1 again has a reduced number of components and thus a more compact design.

In order that the sleeve part 35A of the latching apparatus 35 can be mounted in particular in a twist twist-proof manner in the housing 2 of the lancing device 1, the sleeve part 35A comprises some stay bolts 38 (given a reference numeral only by way of example) and screw tabs 39 (also given a reference numeral only by way of example) (see for example FIGS. 3 and 4), by means of which the latching apparatus 35 can be fastened to the housing 2 in a stationary manner.

The illustration according to FIG. 2 further shows clearly that the fixable tensioning carriage part 26 comprises an inner web 40, an outer web 41 and a gap 42 between them, further in which the sleeve part 32A can be arranged when the lancing device 1 is in the tensioned state 37.

In addition, the sleeve part 35A of the latching apparatus 35, the sleeve part 26A of the fixable tensioning carriage part 26 and the sleeve part 27A of the further tensioning carriage part 27 form a tensioning carriage spring element receiving space 43 in which the tensioning spring carriage element 28 is mounted.

Similarly, the sleeve part 35A of the latching apparatus 35 and the sleeve part 26A of the fixable tensioning carriage part 26, in cooperation with the sleeve part 32A of the axially displaceable lancet holder element 32, form a return spring element receiving space 44.

A lancing spring element receiving space 45 for the lancing spring element 31 is accordingly provided inside the lancing device 1 and is advantageously formed by means of the sleeve part 32A of the axially displaceable lancet holder element 32 and the inner web 40 of the fixable tensioning carriage part 26.

Improved guidance of the lancing spring element 31 is thus achieved in that an inner web plug 46 of reduced diameter of the inner web 40 of the fixable tensioning carriage part 26 also projects in part into the lancing spring element 31.

In order to secure the axially displaceable lancet holder element 32 against unintended premature movement in the lancing direction 18, in particular during tensioning of the lancing device 1 and when a fixable tensioning carriage part 26 is in the tensioning position 36, the axially displaceable lancet holder element 32 comprises a radially elastically bendable finger clip element 47 which can interact axially with an inwardly directed inner collar 48 of the upper shell part 3 when the axially displaceable lancet holder element 32 is slid in the lancing direction 18 by spring force.

This radially elastically bendable finger clip element 47 can be pressed radially inwards in an actuation direction 50 by means of a release pressure element web 49 of the release pressure element 13, whereby it comes free from the inner collar 48 and thus a lancing procedure in the lancing direction 18 can be initiated.

In the region of a lancet receptacle 51, in which the replaceable lancet 12 is held on the axially displaceable lancet holder element 32, the axially displaceable lancet holder element 32 has an outer wall 52 which can likewise strike the inwardly directed inner collar 48 of the upper shell part 3 when the axially displaceable lancet holder element 32 is moved too far counter to the lancing direction 18.

For radially resetting the release pressure element 13, the upper shell part 3 also forms a resilient restoring element 53.

All the sleeve parts 26A, 27A, 32A and 35A are located in the housing in axial alignment in the longitudinal extension 5 of the lancing device 1, resulting in a kinematically particularly simple and thus very reliable design and in this respect a lancing device 1 which is easy to operate.

In this connection, the tensioning carriage spring element 28, the lancing spring element 31 and the return spring element 33 are ideally each designed as compression spring elements in the form of helical springs, whereby the structural design of the present lancing device 1 can be simplified further.

The illustrations according to FIGS. 3 and 4 show very clearly a latching arm element 60 of the latchable latching apparatus 35, which latching arm element can be deflected elastically radially in relation to the axially extending longitudinal axis 6 and thus also in relation to the lancing direction 18, and by means of which the fixable tensioning carriage part 26 can be fixed in the tensioning position 36 to the latching apparatus 35.

In this connection, the elastically deflectable latching arm element 60 extends approximately parallel to the longitudinal axis 6 and extends axially along the outside of the axially displaceable lancet holder element 32.

This elastically deflectable latching arm element 60 comprises at its cantilevered end 61 means 62 for fixing the fixable tensioning carriage part 26, which in this embodiment are in the form of tooth elements 63 and 64.

These tooth elements 63, 64 can interact with a positive fit with counter tooth elements 65 and 66 provided on the fixable tensioning carriage part 26 in the manner of a tongue and groove tooth system (see FIGS. 6, 8 and 9) when the fixable tensioning carriage part 26 is slid axially forwards manually into the tensioning position 36 and the elastically deflectable latching arm element 60 has simultaneously been moved from its free position 67 (see FIGS. 3 and 4) into a locked position 68.

In order to bring about this movement out of the free position 67 (see in particular FIG. 4) and into the locked position 68 (see in particular FIG. 9), the further tensioning carriage part 27 comprises an engagement element 69 in the form of a sliding guide face 70 which in particular is inclined in relation to the longitudinal axis 6 and which can be directed in the lancing direction 18, resting along the elastically deflectable latching arm element 60. In this case, the elastically deflectable latching arm element 60 is bent and accordingly radially engaged.

In order that the elastically deflectable latching arm element 60 can remain in this locked position 68, it latches, with a latching projection element 71, with a positive fit behind a latching rib 72 provided on the axially displaceable lancet holder element 32, in that the latching projection element 71 engages the latching rib 72 from behind.

For this purpose, the elastically deflectable latching arm element 60 is deflectable not only in a first deflection direction 73 (see also FIG. 4) but advantageously additionally also in a further deflection direction 74 (see FIG. 9) which extends at right angles to the first deflection direction 73.

This latching rib 72 which can be engaged radially from behind extends axially on the axially displaceable lancet holder element 32 in the direction of the longitudinal extension 5.

If, when the lancing device 1 is in this tensioned state, the release pressure element 13 is actuated manually, the finger clip element 47 is displaced radially inwards and comes free from the inner collar 48. Owing to the previously tensioned lancing spring element 31, the axially displaceable lancet holder element 32 is then accelerated in the lancing direction 18 and finally reaches a lancing end position 75, as shown in the illustrations according to FIGS. 10 and 11.

At the latest in this lancing end position 75, the latching rib 72 which can be engaged from behind has been moved so far axially forwards in the lancing direction 18 with the axially displaceable lancet holder element 32 that the latching projection element 71 then remains free axially behind the latching rib 72 which can be engaged from behind, since this latching projection element 71 is arranged in an axially stationary manner on the elastically deflectable latching arm element 60.

In this respect, the latching projection element 71 and the latching rib 72 which can be engaged from behind by this latching projection element 71 no longer overlap when the axially displaceable lancet holder element 32 is moving towards the lancing end position 75 or at the latest reaches this lancing end position 75.

As a result, the elastically deflectable latching arm element 60 can move counter to the first deflection direction 73 out of its locked position 68 and into its free position 67 without the elastically deflectable latching arm element 60 having to move counter to the further deflection direction 74.

The tooth elements 63 and 64 are thus then no longer in engagement with the counter tooth elements 65 and 66, and therefore the fixable tensioning carriage element 26 is accelerated from its tensioning position 36 into a rear relaxed position 76 (see FIG. 2).

The latching apparatus is advantageously arranged in the housing 2 such that the latching arm element 60 which is elastically deflectable radially in relation to the lancing direction 18 is arranged such that it can be disengaged radially by a translatory change in position of the axially displaceable lancet holder element 32 in the lancing direction 18, such that the fixable tensioning carriage part 26 is displaced in translation from the tensioning position 36 into the relaxed position 76 with the help of the lancing spring element 31.

The lancing device 1 is then located in the resting position 77 shown in FIGS. 1 and 2 again and can be prepared for a new lancing procedure.

The mechanism described above can also be used when the tensioning slide element 14 is alternatively positioned at the end region 7 as a push button (not shown here) or the like.

It will be understood that the embodiment described above is merely a first configuration of the lancing device according to the invention. In this respect, the configuration of the invention is not limited to this embodiment.

Certain features disclosed in the application are understood to be novel, including for example features either individually or in combination with other features as compared with the prior art.

LIST OF REFERENCE NUMERALS 1 lancing device
2 two-part housing
3 upper shell part
4 lower shell part
5 longitudinal extension
6 longitudinal axis
7 end region
8 head region
9 screw cap
10 feed-through opening
11 lancing needle
12 lancet
13 release pressure element
14 tensioning slide element
15 outer face
16 ejector slide element
17 axial directions
18 lancing direction
19 radial directions
25 tensioning unit
26 fixable tensioning carriage part
26A sleeve part of the fixable tensioning carriage part
27 further tensioning carriage part
27A sleeve part of the further tensioning carriage part
28 tensioning carriage spring element
29 rear starting position
30 drive unit
31 lancing spring element
32 axially displaceable lancet holder element
32A sleeve part of the lancet holder element
33 return spring element
35 latching apparatus
35A sleeve part of the latching apparatus
36 tensioning position
37 tensioned state
38 stay bolts
39 screw tabs
40 inner web
41 outer web
42 gap
43 tensioning carriage spring element receiving space
44 return spring element receiving space
45 lancing spring element receiving space
46 inner web plug
47 finger clip element
48 inner collar
49 release pressure element web
50 actuation direction
51 lancet receptacle
52 outer wall
53 resilient restoring element
60 elastically deflectable latching arm element
61 cantilevered end
62 fixing means
63 front tooth element
64 rear tooth element
65 front counter tooth element
66 rear counter tooth element
67 free position
68 locked position
69 engagement element
70 sliding guide face
71 latching projection face
72 latching rib which can be radially engaged from behind
73 first deflection direction
74 further deflection direction
75 lancing end position
76 relaxed position
77 resting position

We claim:

1. A lancing device for taking blood samples, comprising:
a housing which extends along a longitudinal axis from an end region of the lancing device to a head region of the lancing device,
an axially displaceable lancet holder element for holding a replaceable lancet,
a drive unit comprising at least a lancing spring element for driving the axially displaceable lancet holder element in a lancing direction,
a fixable tensioning carriage part for tensioning said lancing spring element, and
a further tensioning carriage part by which said fixable tensioning carriage part is able to be displaced from a relaxed position at the end region of the lancing device in the lancing direction towards the head region of the lancing device to a tensioning position, wherein said fixable tensioning carriage part is able to be fixed in this tensioning position, wherein by said displacement of the fixable tensioning carriage part the lancing spring element is able to be tensioned, wherein the fixable tensioning carriage part is axially fixed in the tensioning position by means of a latching apparatus which is able to be latched to the axially displaceable lancet holder element, wherein the entire displaceable lancet holder element and the entire fixable tensioning carriage part are displaceable relative to each other along said longitudinal axis, wherein the further tensioning carriage part comprises an engagement element for radial engagement of the latching apparatus which is able to be latched to the axially displaceable lancet holder element.

2. The lancing device according to claim 1, wherein the latching apparatus comprises a latching arm element which can be deflected radially in relation to the lancing direction and which interacts with a positive fit with the axially displaceable lancet holder element during fixing of the fixable tensioning carriage part in the tensioning position.

3. The lancing device according to claim 1, wherein the axially displaceable lancet holder element comprises a latching rib which can be engaged by the latching apparatus and which extends axially on the axially displaceable lancet holder element.

4. The lancing device according to claim 1, wherein the latching apparatus comprises a latching arm element which can be deflected radially in relation to the lancing direction.

5. The lancing device according to claim 4, wherein the latching arm element comprises means for fixing the fixable tensioning carriage part to the latching arm element.

6. The lancing device according to claim 5, wherein the latching apparatus is arranged in the housing such that the latching arm element which can be deflected radially in relation to the lancing direction is arranged such that the latching arm element can be disengaged radially by a translatory change in position of the axially displaceable lancet holder element in the lancing direction, such that the fixable tensioning carriage part can be displaced in translation from the tensioning position into the relaxed position by a compression spring element.

7. The lancing device according to claim 1, wherein the latching apparatus interacts with the fixable tensioning carriage part on a basis of a relative axial position of the axially displaceable lancet holder element in relation to the housing.

8. The lancing device according to claim 1, wherein the latching apparatus comprises a sleeve part which radially surrounds the axially displaceable lancet holder element externally at least in part.

9. The lancing device according to claim 1, wherein the engagement element comprises a sliding guide face which is inclined in relation to the lancing direction.

10. The lancing device according to claim 9 wherein the further tensioning carriage part comprises a sleeve part.

11. The lancing device according to claim 1, wherein the axially displaceable lancet holder element, the fixable tensioning carriage part, or both comprise a sleeve part.

12. The lancing device according to claim 1, wherein in the tensioned state of the lancing device the latching apparatus is latched to the displaceable lancet holder element such that, upon axial displacement of the lancet holder element in the lancing direction, the latching apparatus unlatches and thus the tensioning carriage part fixed to the latching apparatus comes free and is able to be displaced rearwards towards the end region of the lancing device.

13. The lancing device according to claim 1, wherein the lancing device further comprises a release element, wherein in the tensioning position the lancet holder element is fixed against an axial displacement in the lancing direction by direct contact of the lancet holder element to the housing, wherein by a single-stage actuation of the release element the axially displaceable lancet holder element and the fixable tensioning carriage part are releasable in a sequential manner from their respective fixations, wherein in the tensioning position the axially displaceable lancet holder element is initially releasable from its fixation to the housing by the actuation of the release element, wherein the released axially displaceable lancet holder element is displaceable to a lancing end position by the lancing spring element, wherein said displacement of the axially displaceable lancet holder releases the fixation of the fixable tensioning carriage part.

14. A lancing device for taking blood samples, comprising a housing, an axially displaceable lancet holder element for holding a replaceable lancet, a drive unit comprising at least a lancing spring element for driving the axially displaceable lancet holder element in a lancing direction, a fixable tensioning carriage part which is able to be fixed in a tensioning position for tensioning the lancing spring element, and a release element, wherein the fixable tensioning carriage part is axially fixed in the tensioning position by means of a latching apparatus which is able to be latched to the axially displaceable lancet holder element, wherein in the tensioning position the lancet holder element is fixed against an axial displacement in the lancing direction by direct contact of the lancet holder element to the housing, wherein by a single-stage actuation of the release element the axially displaceable lancet holder element and the fixable tensioning carriage part are releasable in a sequential manner from their respective fixations, wherein in the tensioning position the axially displaceable lancet holder element is initially releasable from its fixation to the housing by the actuation of the release element, wherein the released axially displaceable lancet holder element is displaceable to a lancing end position by the lancing spring element, wherein said displacement of the axially displaceable lancet holder releases the fixation of the fixable tensioning carriage part.

15. The lancing device according to claim 14, wherein the axially displaceable lancet holder element comprises a radially elastically bendable finger clip element which is able to interact axially with an inwardly directed inner collar of the housing, to establish the fixation of the lancet holder element to the housing, wherein the finger clip element is displaceable radially inwards by the release element to release the fixation from the inner collar.

16. The lancing device according to claim 14, wherein the latching apparatus comprises a latching arm element which is able to be deflected radially in relation to the lancing direction and comprises means for fixing the fixable tensioning carriage part to the latching arm element.

17. The lancing device according to claim 16, wherein the latching arm element comprises a latching projection element, wherein in the tensioning position the latching projection element latches behind a latching rib provided on the axially displaceable lancet holder element, wherein the latching projection element unlatches from latching rib by the displacement of the axially displaceable lancet holder.

18. The lancing device according to claim 16, wherein the latching apparatus is arranged in the housing such that the latching arm element which is able to be deflected radially in relation to the lancing direction is arranged such that the latching arm element is able to be disengaged radially by a translatory change in position of the axially displaceable lancet holder element in the lancing direction, such that the fixable tensioning carriage part is able to be displaced in translation from the tensioning position into a relaxed position by a compression spring element.

19. A lancing device for taking blood samples, comprising:
 a housing which extends along a longitudinal axis from an end region of the lancing device to a head region of the lancing device,
 an axially displaceable lancet holder element for holding a replaceable lancet,
 a drive unit comprising at least a lancing spring element for driving the axially displaceable lancet holder element in a lancing direction,
 a fixable tensioning carriage part for tensioning said lancing spring element, and
 a further tensioning carriage part by which said fixable tensioning carriage part is able to be displaced from a relaxed position at the end region of the lancing device in the lancing direction towards the head region of the lancing device to a tensioning position,
 wherein said fixable tensioning carriage part is able to be fixed in this tensioning position, wherein by said displacement of the fixable tensioning carriage part the lancing spring element is able to be tensioned,
 wherein the fixable tensioning carriage part is axially fixed in the tensioning position by means of a latching apparatus which is able to be latched to the axially displaceable lancet holder element, wherein the entire displaceable lancet holder element and the entire fixable tensioning carriage part are displaceable relative to each other along said longitudinal axis,
 wherein the latching apparatus comprises a latching arm element which is able to be deflected radially in relation to the lancing direction and comprises means for fixing the fixable tensioning carriage part to the latching arm element.

20. The lancing device according to claim 19, wherein the latching apparatus is arranged in the housing such that the latching arm element which is able to be deflected radially in relation to the lancing direction is arranged such that the latching arm element is able to be disengaged radially by a translatory change in position of the axially displaceable lancet holder element in the lancing direction, such that the fixable tensioning carriage part is able to be displaced in translation from the tensioning position into the relaxed position by a compression spring element.

* * * * *